(12) United States Patent
Guidotti (10) Patent No.: US 7,888,548 B2
(45) Date of Patent: Feb. 15, 2011

(54) ABSORBENT LAYER STRUCTURE

(75) Inventor: Ted Guidotti, Gothenburg (SE)

(73) Assignee: SCA Hygiene Products AB, Gothenburg (SE)

(*) Notice: Subject to any disclaimer, the term of this patent is extended or adjusted under 35 U.S.C. 154(b) by 940 days.

(21) Appl. No.: 11/617,162

(22) Filed: Dec. 28, 2006

(65) Prior Publication Data
US 2007/0112319 A1 May 17, 2007

Related U.S. Application Data

(63) Continuation-in-part of application No. PCT/SE2005/001112, filed on Jul. 4, 2005, which is a continuation-in-part of application No. PCT/SE2004/001077, filed on Jul. 2, 2004.

(51) Int. Cl.
*A61F 13/15* (2006.01)

(52) U.S. Cl. .................. 604/374; 604/375; 604/379; 604/378; 604/368; 604/380; 604/385.101

(58) Field of Classification Search .............. 604/374, 604/375, 379, 378, 368, 380, 385.101
See application file for complete search history.

(56) References Cited

U.S. PATENT DOCUMENTS

| | | | |
|---|---|---|---|
| 3,844,880 A | 10/1974 | Meisel, Jr. et al. | |
| 4,432,833 A | 2/1984 | Breese | |
| 4,610,678 A * | 9/1986 | Weisman et al. | 604/368 |
| 4,673,402 A * | 6/1987 | Weisman et al. | 604/368 |
| 4,699,619 A * | 10/1987 | Bernardin | 604/378 |
| 5,009,650 A | 4/1991 | Bernardin et al. | |
| 5,294,478 A | 3/1994 | Wanek et al. | |
| 5,423,787 A | 6/1995 | Kjellberg | |
| 5,549,589 A * | 8/1996 | Horney et al. | 604/366 |

(Continued)

FOREIGN PATENT DOCUMENTS

EP 1245722 B1 6/2006

(Continued)

OTHER PUBLICATIONS

English translation of relevant portions of an Office Action issued Jul. 30, 2010 in corresponding Columbian Patent Application No. 06130329.

(Continued)

*Primary Examiner*—Jacqueline Stephens
(74) *Attorney, Agent, or Firm*—Buchanan Ingersoll & Rooney PC (57) ABSTRACT

An absorbent layer structure for use as an absorbent body in an absorbent article includes a first surface layer having cellulose fluff pulp, a second surface layer having cellulose fluff pulp, and an inner layer arranged between the surface layers having a mixture of cellulose fluff pulp and 5-90% by weight superabsorbent material, the cellulose fluff pulp in the surface layers having a mat strength which is lower than the mat strength in the inner layer by at least 1 N measured at a weight per unit area of 300 $g/m^2$ and a bulk of 4.5 $cm^3/g$ or less and preferably a mat strength which is lower than the mat strength in the inner layer by at least 2 N measured at a weight per unit area of 300 $g/m^2$ and a bulk of 4.5 $cm^3/g$ or less.

23 Claims, 4 Drawing Sheets

U.S. PATENT DOCUMENTS

| | | |
|---|---|---|
| 5,601,921 A | 2/1997 | Eriksson et al. |
| 5,634,915 A | 6/1997 | Osterdahl |
| 5,741,241 A * | 4/1998 | Guidotti et al. ............. 604/368 |
| 5,866,242 A | 2/1999 | Tan et al. |
| 5,916,670 A | 6/1999 | Tan et al. |
| 5,947,945 A * | 9/1999 | Cree et al. ................. 604/368 |
| 5,961,506 A | 10/1999 | Guidotti |
| 6,080,909 A | 6/2000 | Osterdahl et al. |
| 6,118,042 A | 9/2000 | Palumbo |
| 6,676,649 B2 | 1/2004 | Mizutani |
| 6,703,330 B1 | 3/2004 | Marsh |
| 6,821,383 B2 | 11/2004 | Shore et al. |
| 7,411,110 B2 | 8/2008 | Sawyer et al. |
| 2002/0088574 A1* | 7/2002 | Seltzer et al. ................ 162/72 |
| 2003/0234468 A1 | 12/2003 | Rangachari et al. |
| 2005/0153100 A1* | 7/2005 | Zoller et al. ................ 428/131 |

FOREIGN PATENT DOCUMENTS

| | | |
|---|---|---|
| JP | S50-147112 | 12/1975 |
| JP | S62-104902 | 5/1987 |
| JP | H07-506009 | 7/1995 |
| JP | H08-503397 | 4/1996 |
| JP | H09-507135 | 7/1997 |
| JP | H09-509349 | 9/1997 |
| JP | 2000-083993 | 3/2000 |
| JP | 2000-197656 | 7/2000 |
| JP | 2001-508843 | 7/2001 |
| JP | 2003-026701 | 1/2003 |
| JP | 2003-509162 | 3/2003 |
| JP | 2004-525668 | 8/2004 |
| JP | 3784288 | 6/2006 |
| MX | 9906601 | 4/2000 |
| RU | 2 207 156 | 6/2003 |
| SU | 2 107 118 | 3/1998 |
| WO | 9105106 A1 | 4/1991 |
| WO | WO 93/12275 | 6/1993 |
| WO | WO 93/15702 A | 8/1993 |
| WO | 9819012 A1 | 5/1998 |
| WO | WO 98/58687 | 12/1998 |
| WO | 0066833 A1 | 11/2000 |
| WO | WO 02/49559 A | 6/2002 |

OTHER PUBLICATIONS

English translation of Notice of Reasons for Rejection issued Aug. 24, 2010 in corresponding Japanese Application No. 2007-519174.

Supplemental European Search Report Issued on Mar. 12, 2010, in European Application No. 05 75 7233.

\* cited by examiner

ABSORBENT LAYER STRUCTURE

TECHNICAL FIELD

The invention relates to an absorbent layer structure for use as an absorbent body in an absorbent article. The invention also relates to an absorbent hygiene article, such as a diaper, an incontinence pad or a sanitary towel. The invention can also be applied to absorbent articles such as meat tray liners, bed protectors, chair protectors or the like.

BACKGROUND ART

Absorbent articles such as diapers, incontinence pads, sanitary towels or the like are gradually becoming thinner and thinner. Thin articles are in most cases more flexible and more discreet to wear and are therefore seen as something positive by users. Moreover, they are more compact, which is of course an advantage for transport and storage.

In order for it to be possible to offer thin absorbent articles with retained functioning as far as absorption capacity and leakage security are concerned, the use of different types of highly absorbent materials, what are known as superabsorbents, has become common. Such materials are polymers which are available in the form of particles, fibers or granules and are advantageously incorporated into a fibrous structure, in most cases comprising cellulose fluff pulp.

When superabsorbents are incorporated into a cellulose fibrous structure, however, a number of problems arise.

In order to retain the superabsorbent in the cellulose fluff structure, it is preferable for the fluff structure to be compressed to a high density of the order of 0.1-0.5 g/cm$^3$. Such highly compressed structures feel hard and uncomfortable when they are used in an absorbent article.

Furthermore, fibers attach themselves to rollers and other machine parts during manufacture of the fibrous structures, which results in operational problems.

Moreover, liquid reception and liquid-spreading in a highly compressed material are very slow, which is a particular problem in absorbent articles intended to receive and absorb large quantities of liquid in a short period of time. For example, articles intended for incontinent adults must be capable of taking up several hundred ml of liquid which is discharged at great pressure in the course of ten seconds or so. Instead of being absorbed by the absorbent article, it therefore sometimes happens that the liquid instead flows out over the surface and runs out of the article along the edges and causes leakage. In practice, such an absorbent article may therefore have an actual absorption capacity which is considerably lower than might have been expected from theoretical calculations based on the absorption capacity of the component materials. In order to remedy this problem, use is often made of special liquid-receiving and/or spreading layers. However, such layers increase the thickness of the articles and contribute to a higher production cost owing to greater material consumption and a more complicated manufacturing process.

A modified cellulose fluff pulp produced by means of an oxidation process using nitroxide is previously known from EP 1 245 722. The process increases the degree of "self-crosslinking" between adjacent cellulose fibers and within one and the same cellulose fiber. In this way, an improved network for superabsorbents which are mixed with the modified cellulose fluff pulp is obtained in relation to conventionally cross-linked cellulose fluff pulps.

WO 00/66833 describes another type of modified cellulose fluff pulp where the fibers are provided with a coating of bentonite which prevents bonds between the fibers and reduces the number of fiber knots in the material.

However, a major problem with the treated cellulose fluff pulps is that fiber webs produced from such cellulose fluff pulps have much too low a mat strength to be capable of being handled in continuous manufacturing processes. Moreover, their capacity for retaining superabsorbent particles is still inadequate.

There is therefore a need to produce an absorbent structure with good processability, a high absorption capacity, a good liquid-receiving capacity and great softness and flexibility. Another object of the invention is to offer an absorbent structure with a fiber network of cellulose fibers, which absorbent structure has a good capacity for retaining superabsorbents and for spreading liquid in the absorbent structure.

SUMMARY

An absorbent structure of the kind referred to in the introduction has now been produced. An embodiment of such an absorbent structure is characterized primarily in that it comprises a first surface layer consisting mainly of cellulose fluff pulp, a second surface layer consisting mainly of cellulose fluff pulp, and an inner layer arranged between the surface layers consisting of a mixture of cellulose fluff pulp and 5-90% by weight superabsorbent material, the cellulose fluff pulp in the surface layers having a mat strength which is lower than the mat strength of the inner layer by at least 1 N measured at a weight per unit area of 300 g/m$^2$ and a bulk of 4.5 cm$^3$/g or less and preferably a mat strength which is lower than the mat strength in the inner layer by at least 2 N measured at a weight per unit area of 300 g/m$^2$ and a bulk of 4.5 cm$^3$/g or less.

By combining two layers with different types of cellulose fluff pulp, it is possible for an embodiment of the invention to produce surprisingly improved experienced softness of the absorbent structure. An absorbent structure in accordance with the embodiment of the invention moreover has extremely good processability with regard to both mat strength and reduced fiber adhesion to rollers and other machine parts during manufacture of the absorbent structure.

Moreover, the absorbent structure offers a fiber network for a superabsorbent material which functions extremely well. The fibrous structure provides a compact inner fiber network with a good retaining capacity for a mixed-in superabsorbent even at high superabsorbent contents, up to 90% by weight of the inner layer, and a good liquid-spreading capacity, and also soft outer surfaces with only a slight tendency to adhere to machine parts when the structure is handled in a manufacturing process.

In order to achieve these advantages, only very thin layers, of the order of 0.1-2 mm, of the treated cellulose fluff pulp are required.

DESCRIPTION OF FIGURES

The invention will be described in greater detail below with reference to the figures shown in accompanying drawings, in which.

DESCRIPTION OF PREFERRED EMBODIMENTS

Figure 1:
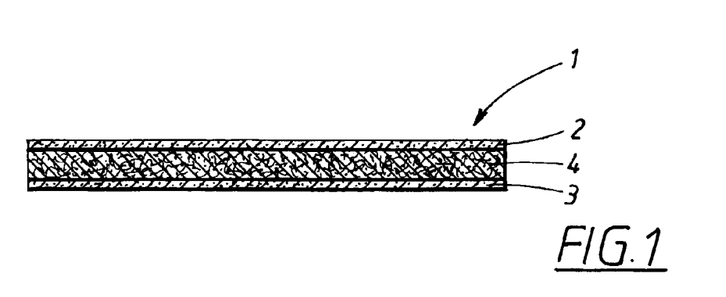
FIG. 1 shows an absorbent layer structure according to an embodiment of the invention.

The absorbent layer structure 1 shown in FIG. 1 comprises a first surface layer 2 comprising cellulose fluff pulp, a second surface layer 3 comprising cellulose fluff pulp, and an inner layer 4 arranged between the surface layers 2, 3 and comprising a mixture of cellulose fluff pulp and 5-80% by weight superabsorbent material. The mixture is preferably an essentially homogeneous mixture, so that the superabsorbent material is uniformly distributed in the inner layer 4.

The superabsorbent material is preferably present in particle form, but granules, flakes or fibers can also be used within the scope of the invention. Superabsorbent materials are polymers with a capacity for absorbing several times their own weight of water or body fluid while forming an aqueous gel. The superabsorbent material can be of one single type or consist of a mixture of two or more superabsorbents which differ as far as absorption rate, particle size, gel strength, chemical composition or other properties are concerned. For example, there are superabsorbents with different absorption capacity at different temperatures or at different pH values.

The cellulose fluff pulp in the inner layer 4 is preferably untreated chemical cellulose fluff pulp (CP) with a bulk (excluding the superabsorbent material) of at most 4.5 cm$^3$/g. The inner layer 4 preferably has a thickness of 0.3-5 mm, more preferably 0.5-2 mm and most preferably roughly 1.2-1.6 mm. The two surface layers 2, 3 can comprise the same or different cellulose fluff pulps. The cellulose fluff pulp in the surface layers 2, 3 is preferably a chemical cellulose fluff pulp which has been treated in order to reduce fiber-fiber bonds in the material. Such treatment can be brought about by coating the fibers with a debonding substance, such as various types of inorganic salts, for example aluminium salt, or mineral fillers such as clay, lime, carbonate, talc or microparticles of bentonite in accordance with WO 00/66833. Fibers treated in the way described in EP 1 245 722, that is to say by means of an oxidation process using nitroxide, can also be used for the surface layers. 6. Further examples of useful debonders are found in U.S. Pat. No. 3,844,880, U.S. Pat. No. 4,432,833 and WO 98/19012. The debonders mentioned in these documents include quarternary ammonium compounds, bis-imidazolinium compounds, di-quarternary ammonium compounds, polyammonium compounds, phospholipids, silicone quarternaries, organoreactive polysiloxanes and silicone glycols.

The surface layers 2, 3 preferably have a bulk of 3 cm$^3$/g or more and a thickness of 0.05-1.0 mm, more preferably 0.1-0.5 mm and most preferably 0.2-0.3 mm.

The entire absorbent structure preferably has a thickness of at most 8 mm, more preferably at most 5 mm and most preferably at most 2 mm. The weight per unit area of the absorbent structure is preferably 300-2000 g/m$^2$, more preferably 500-1500 g/m$^2$ and most preferably 800-1200 g/m$^2$.

Figure 2:
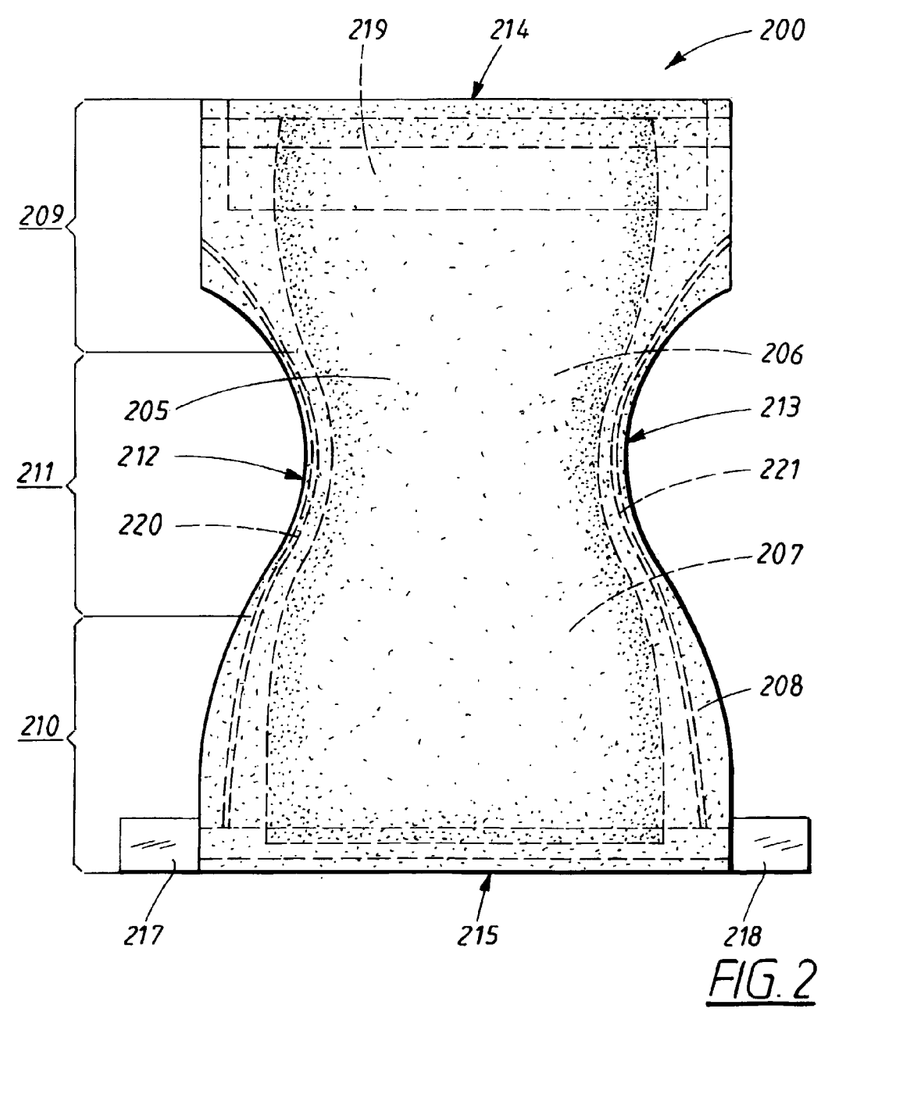
FIG. 2 shows a diaper comprising a layer structure according to an embodiment of the invention.

FIG. 2 shows a diaper 200 of fairly simple construction. It is of course possible to use additional components, such as raised leakage barriers, shape-stabilizing elements, liquid-receiving layers or the like. The diaper 200 shown in FIG. 2 comprises a first, liquid-permeable surface layer 205, a second, liquid-impermeable surface layer 206, and an absorbent body 207 arranged between the surface layers 205, 206. The two surface layers 205, 206 extend beyond the absorbent body 207 around its entire periphery. The surface layers 205, 206 are interconnected within the extending portions 208 by gluing, or welding using heat or ultrasound.

The liquid-permeable surface layer 205 can consist of any material known for the purpose such as a layer of non-woven material, perforated plastic film, net material or the like. The surface layer 205 can of course also consist of a laminate of two or more layers of the same material or different materials.

The liquid-impermeable surface layer 206 can consist of a liquidtight plastic film, a non-woven layer which has been coated with a liquid-blocking material, a laminate of non-woven and plastic film or another flexible material capable of resisting liquid penetration. It may be an advantage, however, if the liquid-impermeable surface layer 206 has a certain breathability, that is to say allows water vapour to pass through the layer 206.

The diaper 200 has an elongate shape, with wider front and rear portions 209, 210 and a narrower, intermediate crotch portion 211. The front portion 209 is that part of the diaper 200 which is intended to face forwards on the wearer when the diaper is being used, and the rear portion 210 is that part of the diaper 200 which faces backwards on the wearer. The diaper 200 also has two longitudinal, inwardly curved side edges 212, 213, a front edge 214 and a rear edge 215.

The diaper 200 is of the kind which is fastened together when it is used, so that it surrounds the lower part of the abdomen of the wearer in a pant-like manner. For this purpose, a fastening tab 217, 218 is arranged projecting from each side edge 212, 213, close to the rear edge 215 of the diaper. The fastening tabs 217, 218 are intended to interact with a receiving area 219 arranged on the liquid-impermeable surface layer 206 on the front portion 209 of the diaper 200. Such a receiving area 219 is arranged so as to interact with fastening elements on the fastening tabs 217, 218. Commonly used fastening elements are hook and loop surfaces or self-adhesive glue. In the first case, hook elements are in most cases arranged on the fastening tabs 217, 218, while the receiving area 219 comprises some form of loop element, for example non-woven. In the second case, the adhesive on the fastening tabs 217, 218 is arranged so as to adhere to a usually reinforced plastic surface on the outside of the diaper 200. It is of course possible to use alternative fastening elements, such as buttons and buttonholes, hooks and eyes, press studs or the like.

The diaper 200 is also provided with longitudinal elastic elements 220, 221, applied in a pretensioned state, along the side edges 212, 213 of the diaper. The elastic elements 220, 221 are arranged so as to curve the diaper 200 according to the body of the wearer during use and at the same time constitute the leg elastic of the diaper. In this way, the elastic elements 220, 221 serve to hold the side edges 212, 213 of the diaper in sealing contact with the legs of the wearer so as to counteract gaps appearing between the diaper and the body of the wearer during use, through which body fluid can leak out of the diaper.

The absorbent body 207 comprises an hourglass-shaped layer of the absorbent structure according to the invention. The absorbent body 207 therefore comprises a laminate comprising two thinner layers of treated cellulose fluff pulp which are arranged on each side of an inner layer of untreated, greatly compressed cellulose fluff pulp with 5-80% superabsorbent and preferably 15-35% superabsorbent mixed in.

The construction shown provides an absorbent article which functions well for many applications, with a good absorption capacity, great flexibility and a high degree of experienced softness. As the absorbent structure according to an embodiment of the invention can be made very thin, with a preferable thickness around roughly 2 mm, this means that a diaper according to an embodiment of the invention, with the simple construction shown in FIG. 2, can have a total thickness which is less than 2.5 mm.

If further absorption capacity is required, the absorbent structure can be made thicker, or alternatively a number of absorbent structures according to embodiments of the invention can be placed one on another. The absorbent structure according to an embodiment of the invention can also be combined with other absorbent layers. For example, it may be desirable to place a layer with a very great absorption capacity and liquid-retaining capacity below the absorbent structure according to an embodiment of the invention, that is to say on that side of the absorbent structure which faces the liquid-impermeable surface layer 206. It may also be desirable to arrange a liquid-receiving layer immediately inside the liquid-permeable surface layer 205, between it and the absorbent body 207. Such a liquid-receiving layer is usually a layer of bonded or unbonded fiber wadding, a latex-bonded cellulose material or the like.

The invention can of course be applied to other variants of diapers, such as pant diapers, belted diapers or the like, and also to all kinds of incontinence pad. A pant diaper means a diaper which is supplied to the user in the form of assembled absorbent pants. A belted diaper is a diaper which is supported by a separate or integrated waist belt. Here, incontinence pads mean absorbent articles intended to be supported in the crotch portion of a pair of briefs.

Figure 3:
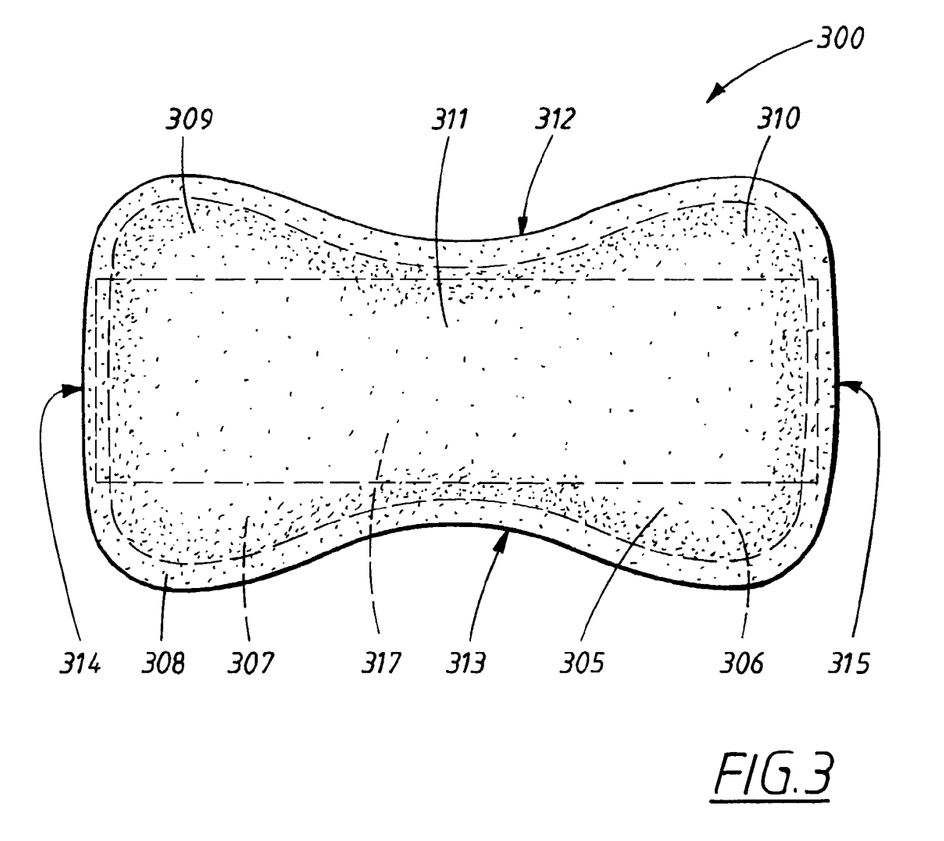
FIG. 3 shows a sanitary towel comprising a layer structure according to an embodiment of the invention.

The sanitary towel 300 shown in FIG. 3 is shown from the side which is intended to face the underwear of the wearer when the towel is being worn. The sanitary towel 300 comprises a liquid-permeable surface layer 305, arranged on that side of the sanitary towel 300 which is intended to face the wearer during use, a liquid-impermeable surface layer 306, arranged on that side of the sanitary towel 300 which is intended to face away from the wearer during use, and an absorbent body 307 enclosed between the two surface layers 305, 306.

The material of the liquid-permeable surface layer 305 can be, for example, a perforated plastic film, a net made of plastic or textile material, a non-woven material or a laminate consisting of, for example, a perforated plastic layer and a non-woven layer. The plastic is usually a thermoplastic, such as polyethylene or polypropylene. Suitable non-woven materials can be made of natural fibers, such as cellulose or cotton, or of synthetic fibers, such as polyethylene, polypropylene, polyester, polyurethane, nylon or regenerated cellulose. It is of course also possible to use non-woven materials made from fiber mixtures.

It is not necessary for the liquid-permeable surface layer 305 actually to comprise a separate material layer. For example, the liquid-permeable covering layer can constitute an integrated part of the absorbent body 307. Use can therefore be made of an absorbent non-woven material, which can be included as a component in the absorbent body 307 and at the same time constitute a liquid-permeable surface layer. Such constructions are not uncommon in very thin towels and panty liners.

The liquid-impermeable surface layer 306 comprises a liquid-impermeable material. Thin, liquidtight plastic films are suitable for the purpose. However, it is also possible to use materials which are originally liquid-permeable but have been provided with a coating of plastic, resin or other sealing material. In this way, leakage of liquid from the underside of the absorbent article is prevented. The liquid-impermeable surface layer 306 can therefore comprise any material which is skin-friendly and meets the liquid-impermeability criterion. Examples of materials suitable as a barrier layer are plastic films, non-woven materials and various types of laminate. Plastic films which can be used are, for example, those made of polyethylene, polypropylene or polyester. Alternatively, the liquid-impermeable surface layer 306 can comprise a laminate made of a liquid-impermeable plastic layer facing the absorbent body and a non-woven layer facing the underwear of the wearer. Such a construction provides a leakproof barrier layer with a textile feel.

The two surface layers 305, 306 are interconnected outside the absorbent body 307 and form an extending edge 308 around the entire periphery of the sanitary towel 300. The surface layers can be joined together in any suitable way, such as by adhesive, sewing or welding using heat or ultrasound.

The sanitary towel 300 is essentially hourglass-shaped and has two end portions 309, 310 and an intermediate narrower crotch portion 311 intended to be arranged between the legs of the wearer. The sanitary towel 300 also has two inwardly curved side edges 312, 313 and two outwardly curved end edges 314, 315.

The sanitary towel 300 is provided with an adhesive fastening element 317 in the form of a strand of adhesive which is attached in the crotch portion of the briefs of the wearer when the towel 300 is worn. Before use, the fastening element 317 is protected in a conventional way by a detachable protective strip which is removed when the adhesive is to be exposed for fastening. The fastening element 317 shown is only an example of the design of an adhesive fastening element. Other patterns and positions of fastening elements are of course possible.

As in the case of the diaper 200 shown in FIG. 2, the absorbent body 307 comprises an hourglass-shaped layer of an absorbent structure according to an embodiment of the invention. The absorbent body 307 therefore comprises a laminate comprising two thinner layers of treated cellulose fluff pulp arranged one on each side of an inner layer of untreated, greatly compressed cellulose fluff pulp with 5-80% superabsorbent and preferably 15-35% superabsorbent mixed in.

In most cases, sufficient absorption capacity is provided with a single layer of the absorbent structure according to an embodiment of the invention. The resultant sanitary towel 300 has great flexibility and a high degree of experienced softness. Sanitary towel development has moved towards thinner and thinner products which can be attached inside the briefs of the wearer in a conformable way and provide great discreetness and comfort when worn. As the absorbent structure according to an embodiment of the invention can be made very thin, with a suitable thickness around roughly 2 mm, this means that a sanitary towel according to an embodiment of the invention, with the simple construction shown in FIG. 3, can have a total thickness which is less than 2.5 mm.

If further absorption capacity is required, the absorbent structure can be made thicker, or alternatively a number of absorbent structures according to the invention can be placed one on another. The absorbent structure according to an embodiment of the invention can also be combined with further absorbent layers. It may also be desirable to arrange a liquid-receiving layer immediately inside the liquid-permeable surface layer 305, between it and the absorbent body 307.

The invention can of course be applied to other absorbent articles intended to be attached inside the briefs of a wearer, such as incontinence pads and panty liners. Such sanitary towels, incontinence pads and panty liners can of course comprise other components apart from those described above, such as fastening wings, raised portions, textile edges, side edge barriers or the like.

Test Method

Determining Mat Strength

Mat strength means the strength of an absorbent body made of defibered pulp. The idea behind the measurement is to determine the force required for a bursting body to pass through the pulp specimen at a constant speed, e.g., 50 m/min.

Figure 4:
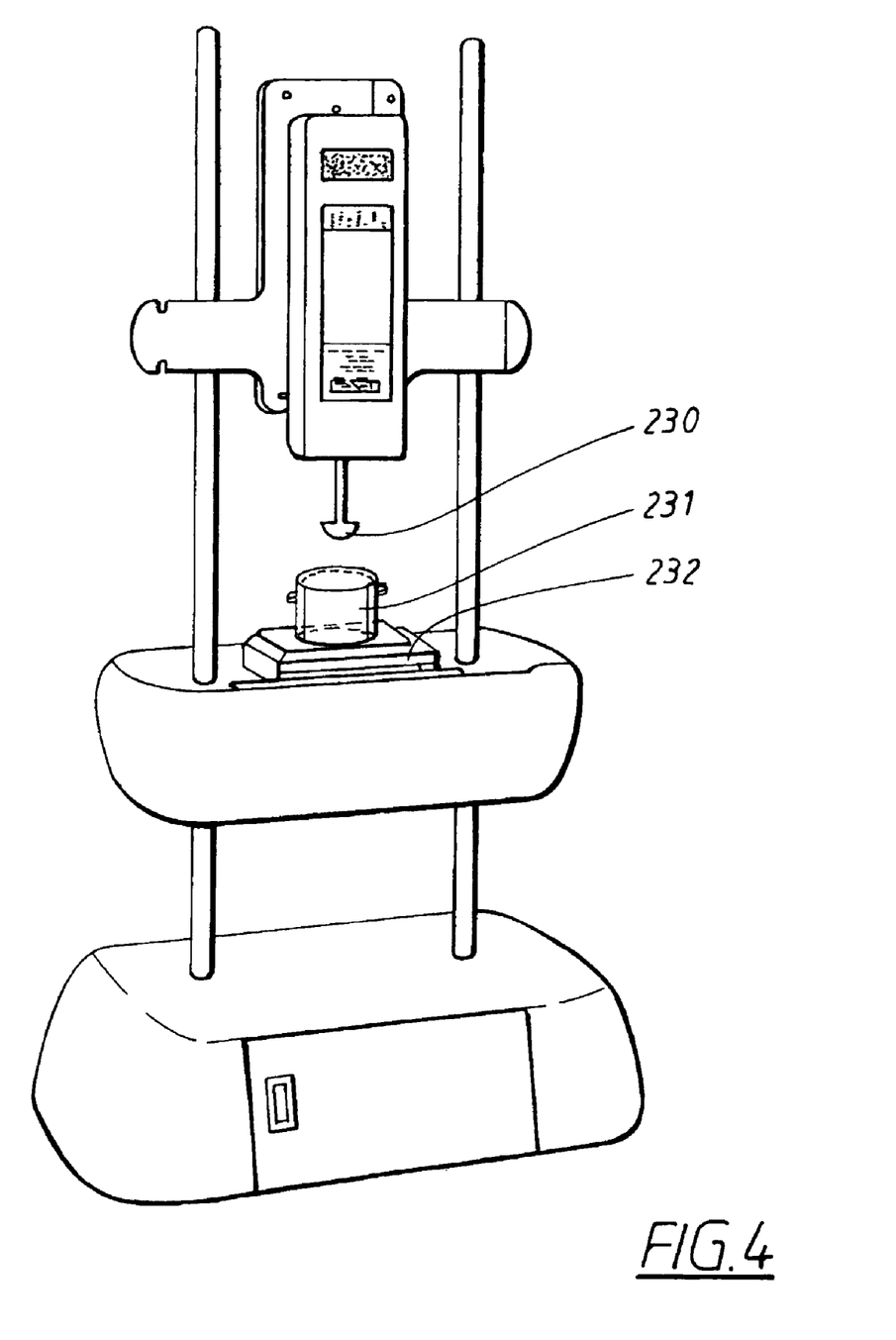
FIG. 4 shows measuring equipment for determining mat strength.
Figure 5:
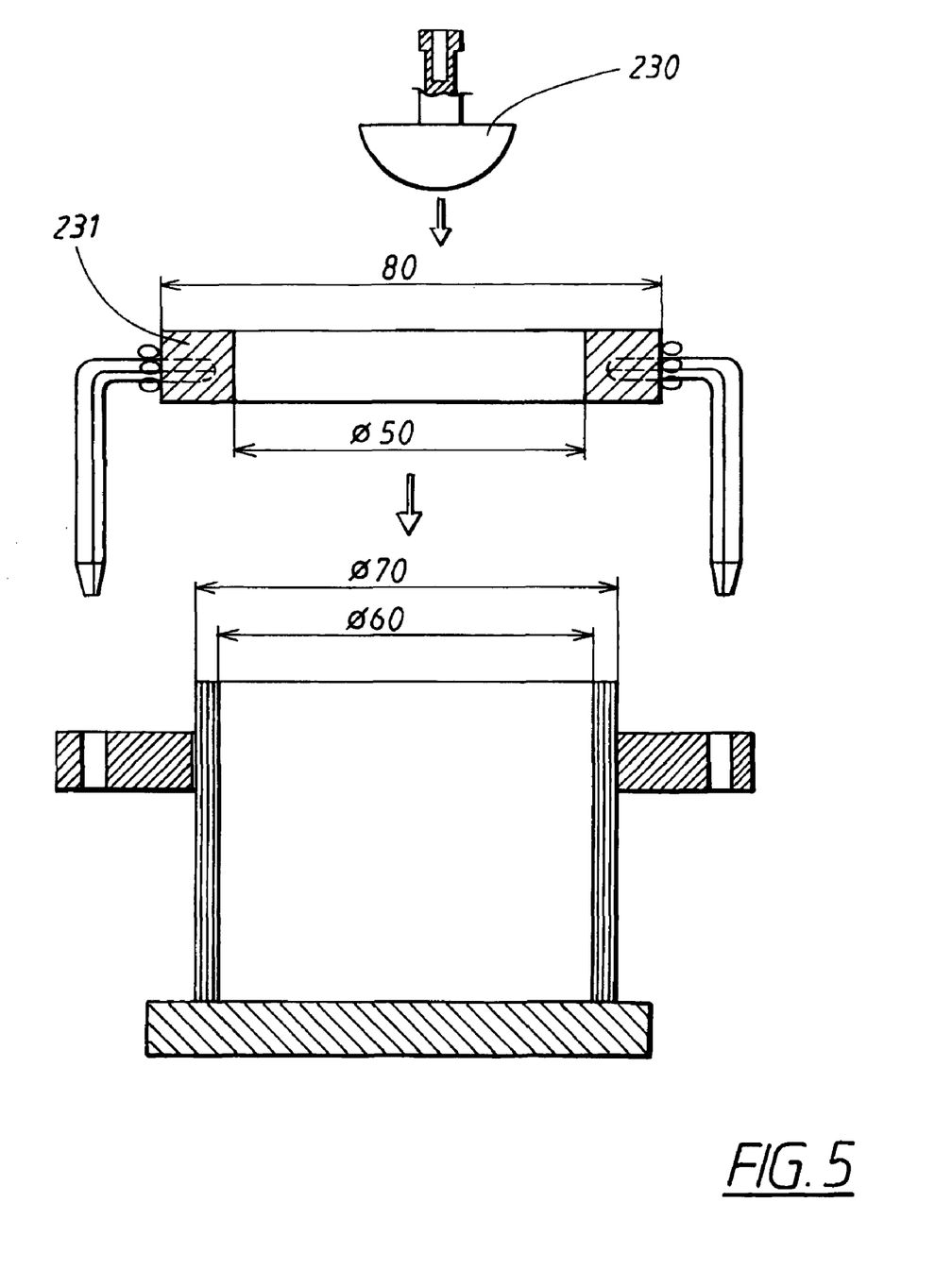
FIG. 5 shows a section through a part of the measuring equipment in FIG. 4.

The apparatus is as shown in FIGS. 4 and 5 and comprises:

a bursting body 230 a specimen holder 231 a balance 232 with measuring accuracy of 0.01 g a thickness gauge with a measuring foot of 20 cm² and a force of 1N (0.5 kPa)

a punch with an 80×80 mm punching tool a ruler with 1 mm measuring accuracy

Specimen Preparation:

Number of specimens measured for each determination was five (5).

A specimen of a size of 80×80 mm was punched out of the pulp mat tested.

The thickness (t) of the specimen was determined with an accuracy of 0.01 cm.

The weight (m) of the specimen was determined with an accuracy of 0.1 g.

The specimen was handled carefully with the aid of a thin plate.

Determination of weight, thickness and bursting strength of the specimen is to be carried out directly after taking the specimen.

From the values obtained, the values for bulk, weight per unit area and density can then be calculated. The measurements were performed on specimens conditioned for 24 hours at 23° C. (+/−1° C.) and a relative humidity of 50% (+/−3%).

Procedure:

The specimen was fastened in the specimen holder 231. The specimen holder 231 and the bursting body 230 were mounted in the apparatus (see FIG. 1). The test was started. The maximum force (F) on bursting was recorded.

Calculation and Presentation of Results:

| Specimen thickness | t  | (cm)      |
|--------------------|----|-----------|
| Specimen weight    | m  | (g)       |
| Specimen area      | A  | (dm²)     |
| Specimen length    | l  | (cm)      |
| Specimen width     | w  | (cm)      |
| Mat strength       | F  | (N)       |
| Bulk               | B  | (cm³/g)   |
| Bursting factor    | BF | (N dm²/g) |

$$B = \frac{A \times 100 \times t}{m} = \frac{l \times w \times t}{m} \; (cm^3/g)$$

$$BF = \frac{F \times A}{m} = \frac{F \times l \times t}{m \times 100} \; (N\,dm^2/g)$$

The report indicates: mean value
maximum value
minimum value

Accuracy:

Mat strength 0.1 N

Bursting strength 0.01 N dm²/g

Mat strength bulk 0.5 cm³/g

Example 1

Cellulose fluff pulp from Weyerhaeuser. American Southern Pine, untreated pulp with designation NB416.

Example 2

American Southern Pine cellulose fluff pulp treated as indicated in EP 1 245 722, treated in accordance with the invention.

Example 3

Cellulose fluff pulp from Weyerhaeuser. American Southern Pine, pulp with designation TR934A, treated in accordance with the invention.

The results of the measurements conducted on specimens according to Examples 1-3 at four different bulk values (3 cm³/g, 4.5 cm³/g, 6 cm³/g, and 10 cm³/g) are presented in Tables 1-3.

Bulk (B) is determined by first measuring the thickness of the layer using a measurement gauge that exerts a pressure of 0.5 kPa with a foot having an area of about 1600 mm². All thicknesses and bulks are determined after the sample has been conditioned for about 24 hours at 23 degrees C and 50% relative humidity.

Determination of Pulp Bulk

Pulp bulk is defined as the bulk of the pulp, $B_{pulp}$. That is, volume occupied by pulp [cm³], i.e. excluding the volume that is occupied by super absorbents, divided by the weight of the pulp [g].

t: Sample thickness [cm]

bw: Basis weight [g/cm²]

$\rho_{SAP}$: Bulk density of SAP according to Edana WSP 260.2 (05) [g/cm³]

Indices pulp and SAP refers to the respective materials.

$$B_{pulp} = \frac{t - (bw_{SAP}/\rho_{SAP})}{bw_{pulp}} \; [cm^3/g]$$

Example:

Thickness=0.14 cm gscm Pulp=0.03 gscm SAP=0.015

$\rho_{SAP}$=0.625

Pulp Bulk=(0.14−0.015/0.625)/0.03

Pulp Bulk=3.87 cm³/g

It is also preferable that the sample have not only an average of 300 g/m³ basis weight, but that the fibers are evenly distributed so that the variation of basis weight within the sample is at a good level. One standard for this is the coefficient of variation (CV), and is defined as the standard deviation of 1320 mm samples divided by the average weight of all samples. The CV should be equal to or less than 10% for samples with an area of about 1320 mm². The small samples are taken from different parts of many larger 80 mm×80 mm samples. For example, the small samples are cut out from the left side, the middle, the right side, the front, the back etc. of the larger 80 mm×80 mm samples.

At least 30 samples should be weighed. The weight of each small sample should be recorded with an accuracy of 0.01 g. As a result, material with a CV less than 10%, is evenly distributed.

As this is a destructive method it can be assumed that if typical small samples have a CV under 10% that the basis weight variation of all larger samples will be acceptable.

TABLE 1

(Example 1)

| Specimen no. | Weight (g) | Thickness (mm) | Weight per unit area (g/m$^2$) | Bulk (cm$^3$/g) | Density (kg/m$^3$) | Mat strength (N) |
|---|---|---|---|---|---|---|
| 1 | 1.98 | 0.90 | 309 | 2.9 | 344 | 3.92 |
| 2 | 2.00 | 0.94 | 313 | 3.0 | 332 | 5.12 |
| 3 | 2.02 | 0.93 | 316 | 2.9 | 339 | 5.28 |
| 4 | 1.98 | 0.89 | 309 | 2.9 | 348 | 5.69 |
| 5 | 2.03 | 0.95 | 317 | 3.0 | 334 | 4.40 |
| Mean | 2.00 | 0.92 | 313 | 2.9 | 339 | 4.9 |
| Min. | 1.98 | 0.89 | 309 | 2.9 | 332 | 3.9 |
| Max. | 2.03 | 0.95 | 317 | 3.0 | 348 | 5.7 |
| 1 | 2.08 | 1.47 | 325 | 4.5 | 221 | 3.56 |
| 2 | 2.01 | 1.38 | 314 | 4.4 | 228 | 2.95 |
| 3 | 2.07 | 1.44 | 323 | 4.5 | 225 | 4.08 |
| 4 | 1.96 | 1.35 | 306 | 4.4 | 227 | 3.75 |
| 5 | 2.06 | 1.44 | 322 | 4.5 | 224 | 4.47 |
| Mean | 2.04 | 1.42 | 318 | 4.5 | 225 | 3.8 |
| Min. | 1.96 | 1.35 | 306 | 4.4 | 221 | 3.0 |
| Max. | 2.08 | 1.47 | 325 | 4.5 | 228 | 4.5 |
| 1 | 2.08 | 1.91 | 325 | 5.9 | 170 | 2.15 |
| 2 | 1.98 | 1.81 | 309 | 5.9 | 171 | 1.87 |
| 3 | 2.10 | 1.94 | 328 | 5.9 | 169 | 1.89 |
| 4 | 1.98 | 1.88 | 309 | 6.1 | 165 | 1.54 |
| 5 | 2.03 | 1.94 | 317 | 6.1 | 163 | 1.81 |
| Mean | 2.03 | 1.90 | 318 | 6.0 | 168 | 1.9 |
| Min. | 1.98 | 1.81 | 309 | 5.9 | 163 | 1.5 |
| Max. | 2.10 | 1.94 | 328 | 6.1 | 171 | 2.2 |
| 1 | 2.05 | 3.18 | 320 | 9.9 | 101 | 1.46 |
| 2 | 2.02 | 3.14 | 316 | 9.9 | 101 | 1.46 |
| 3 | 2.06 | 3.19 | 322 | 9.9 | 101 | 1.41 |
| 4 | 2.01 | 3.13 | 314 | 10.0 | 100 | 1.37 |
| 5 | 2.00 | 3.09 | 313 | 9.9 | 101 | 1.27 |
| Mean | 2.03 | 3.15 | 317 | 9.9 | 101 | 1.4 |
| Min. | 2.00 | 3.09 | 313 | 9.9 | 100 | 1.3 |
| Max. | 2.06 | 3.19 | 322 | 10.0 | 101 | 1.5 |

TABLE 2

(Example 2)

| Specimen no. | Weight (g) | Thickness (mm) | Weight per unit area (g/m$^2$) | Bulk (cm$^3$/g) | Density (kg/m$^3$) | Mat strength (N) |
|---|---|---|---|---|---|---|
| 1 | 1.96 | 0.95 | 306 | 3.1 | 322 | 3.55 |
| 2 | 2.02 | 0.97 | 316 | 3.1 | 325 | 3.86 |
| 3 | 2.06 | 0.94 | 322 | 2.9 | 342 | 3.59 |
| 4 | 1.97 | 0.94 | 308 | 3.1 | 327 | 2.58 |
| 5 | 2.06 | 1.00 | 322 | 3.1 | 322 | 3.26 |
| Mean | 2.01 | 0.96 | 315 | 3.1 | 328 | 3.4 |
| Min. | 1.96 | 0.94 | 306 | 2.9 | 322 | 2.6 |
| Max. | 2.06 | 1.00 | 322 | 3.1 | 342 | 3.9 |
| 1 | 2.03 | 1.39 | 317 | 4.4 | 228 | 4.10 |
| 2 | 2.03 | 1.40 | 317 | 4.4 | 227 | 2.16 |
| 3 | 1.96 | 1.36 | 306 | 4.4 | 225 | 2.15 |
| 4 | 1.97 | 1.40 | 308 | 4.5 | 220 | 2.11 |
| 5 | 1.97 | 1.38 | 308 | 4.5 | 223 | 2.36 |
| Mean | 1.99 | 1.39 | 311 | 4.5 | 225 | 2.6 |
| Min. | 1.96 | 1.36 | 306 | 4.4 | 220 | 2.1 |
| Max. | 2.03 | 1.4 | 317 | 4.5 | 228 | 4.1 |
| 1 | 2.01 | 1.90 | 314 | 6.0 | 165 | 1.95 |
| 2 | 1.96 | 1.80 | 306 | 5.9 | 170 | 1.55 |
| 3 | 2.00 | 1.84 | 313 | 5.9 | 170 | 1.60 |

TABLE 2-continued (Example 2)

| Specimen no. | Weight (g) | Thickness (mm) | Weight per unit area (g/m$^2$) | Bulk (cm$^3$/g) | Density (kg/m$^3$) | Mat strength (N) |
|---|---|---|---|---|---|---|
| 4 | 2.03 | 1.88 | 317 | 5.9 | 169 | 1.92 |
| 5 | 1.96 | 1.85 | 306 | 6.0 | 166 | 1.59 |
| Mean | 1.99 | 1.85 | 311 | 6.0 | 168 | 1.7 |
| Min. | 1.96 | 1.8 | 306 | 5.9 | 165 | 1.6 |
| Max. | 2.03 | 1.9 | 317 | 6.0 | 170 | 2.0 |
| 1 | 1.99 | 3.08 | 311 | 9.9 | 101 | 1.22 |
| 2 | 1.95 | 3.04 | 305 | 10.0 | 100 | 1.13 |
| 3 | 1.95 | 3.07 | 305 | 10.1 | 99 | 1.28 |
| 4 | 1.93 | 3.05 | 302 | 10.1 | 99 | 1.30 |
| 5 | 1.95 | 3.07 | 305 | 10.1 | 99 | 1.37 |
| Mean | 1.95 | 3.06 | 305 | 10.0 | 100 | 1.3 |
| Min. | 1.93 | 3.04 | 302 | 9.9 | 99 | 1.1 |
| Max. | 1.99 | 3.08 | 311 | 10.1 | 101 | 1.4 |

TABLE 3

(Example 3)

| Specimen no. | Weight (g) | Thickness (mm) | Weight per unit area (g/m$^2$) | Bulk (cm$^3$/g) | Density (kg/m$^3$) | Mat strength (N) |
|---|---|---|---|---|---|---|
| 1 | 2.02 | 0.96 | 316 | 3.0 | 329 | 1.07 |
| 2 | 2.03 | 0.98 | 317 | 3.1 | 324 | 1.53 |
| 3 | 1.97 | 0.95 | 308 | 3.1 | 324 | 1.18 |
| 4 | 1.93 | 0.88 | 302 | 2.9 | 343 | 1.23 |
| 5 | 1.98 | 0.91 | 309 | 2.9 | 340 | 1.52 |
| Mean | 1.99 | 0.94 | 310 | 3.0 | 332 | 1.3 |
| Min. | 1.93 | 0.88 | 302 | 2.9 | 324 | 1.1 |
| Max. | 2.03 | 0.98 | 317 | 3.1 | 343 | 1.5 |
| 1 | 2.00 | 1.39 | 313 | 4.4 | 225 | 1.40 |
| 2 | 1.98 | 1.41 | 309 | 4.6 | 219 | 1.09 |
| 3 | 1.94 | 1.37 | 303 | 4.5 | 221 | 1.16 |
| 4 | 2.04 | 1.41 | 319 | 4.4 | 226 | 1.44 |
| 5 | 2.00 | 1.41 | 313 | 4.5 | 222 | 1.26 |
| Mean | 1.99 | 1.40 | 311 | 4.5 | 223 | 1.3 |
| Min. | 1.94 | 1.37 | 303 | 4.4 | 219 | 1.1 |
| Max. | 2.04 | 1.41 | 319 | 4.6 | 226 | 1.4 |
| 1 | 1.99 | 1.81 | 311 | 5.8 | 172 | 0.77 |
| 2 | 1.98 | 1.88 | 309 | 6.1 | 165 | 0.87 |
| 3 | 1.96 | 1.82 | 306 | 5.9 | 168 | 0.81 |
| 4 | 2.02 | 1.93 | 316 | 6.1 | 164 | 0.95 |
| 5 | 1.99 | 1.82 | 311 | 5.9 | 171 | 0.88 |
| Mean | 1.99 | 1.85 | 311 | 6.0 | 168 | 0.9 |
| Min. | 1.96 | 1.81 | 306 | 5.8 | 164 | 0.8 |
| Max. | 2.02 | 1.93 | 316 | 6.1 | 172 | 1.0 |
| 1 | 2.02 | 3.11 | 316 | 9.9 | 101 | 1.05 |
| 2 | 2.00 | 3.10 | 313 | 9.9 | 101 | 0.87 |
| 3 | 1.99 | 3.06 | 311 | 9.8 | 102 | 0.86 |
| 4 | 1.99 | 3.08 | 311 | 9.9 | 101 | 0.86 |
| 5 | 2.02 | 3.10 | 316 | 9.8 | 102 | 0.82 |
| Mean | 2.00 | 3.09 | 313 | 9.9 | 101 | 0.9 |
| Min. | 1.99 | 3.06 | 311 | 9.8 | 101 | 0.8 |
| Max. | 2.02 | 3.11 | 316 | 9.9 | 102 | 1.1 |

As emerges from the measurement results in the tables, the nature of the pulp has an effect on mat strength. There is a great difference in the mat strength of cellulose fluff pulp layers according to the pulp of example 1 in comparison with the pulps of examples 2 and 3 at low bulk/high density. This means that cellulose fluff pulp according to examples 2 and 3 generally results in a mat with poor cohesive capacity even after great compression. As a result of the relationship between the fiber and the superabsorbent particles, there may not be good superabsorbent particle binding and fixation within the layer. It will thus have a poor capacity for retaining superabsorbents in the fibrous structure.

In the foregoing examples, the pulp of example 1 is suitable for the inner layer, and the pulps of examples 2 and 3 are suitable for the outer layers.

The present invention is not limited to structures wherein the layers are within about 10 percent of 300 g/m$^2$. According to the present invention, the selection of the pulp that is used to make the mat is important. Although the foregoing tests are made by measuring a mat, the nature of the pulp has an effect on the test results. In order to obtain relevant test results, if an absorbent structure has a layer that is not within about 10 percent of 300 g/m$^2$, each of the layers should have similar basis weights, e.g., within +/−10% of each other, and a CV of less than 10%. If a layer in a structure to be tested does not have the proper basis weight, density, and/or CV for measuring according to the foregoing test methods, the pulp in the layer can be reassembled into a layer that does have proper specifications. Since it is the nature of the pulp that is most important, the fact that the layer is reconstructed into different dimensions should not be a significant factor.

Furthermore, if a structure has layers that have a bulk less than 4.5 cm$^3$/g, for proper testing, each of the samples to be measured must have a comparable bulk. For example, if one of the samples has a bulk of about 3.5 cm$^3$/g, then the other layers must have a similar bulk, e.g., 3.5 cm$^3$/g plus or minus 5%.

While the invention has been described with reference to a particular embodiment, it will be understood that the present invention is by no means limited to the particular constructions and methods herein disclosed and/or shown in the drawings, but also comprises any modifications or equivalents within the spirit and scope of the claims.

The invention claimed is:

1. An absorbent article including an absorbent layer structure for use as an absorbent body in an absorbent article, the absorbent layer structure comprising:
    a first surface layer comprising cellulose fluff pulp;
    a second surface layer comprising cellulose fluff pulp; and
    an inner layer arranged between the first and second surface layers, the inner layer comprising a mixture of cellulose fluff pulp and 5-90% by weight superabsorbent material;
    wherein the cellulose fluff pulp in the first and second surface layers has a mat strength which is lower than the mat strength of the inner layer by at least 1 N when all three layers are measured at a weight per unit area equal to or about 300 g/m$^2$ and a bulk equal to or about 4.5 cm$^3$/g, and the weight per unit area of each measured layer is within 10% of each layer and the bulk of each measured layer is within 10% of each layer, and
    the cellulose fibers in at least one of the surface layers have a coating of a substance which reduces the number of fiber-fiber bonds in the cellulose fluff pulp.

2. The absorbent article according to claim 1, wherein the cellulose fluff pulp in the first and second surface layers has a mat strength which is lower than the mat strength of the inner layer by at least 2 N when all three layers are measured at a weight per unit area within ten percent of 300 g/m$^2$ and a bulk of 4.5 cm$^3$/g or less.

3. The absorbent article according to claim 1, wherein the cellulose fluff pulp in the first and second surface layers has a mat strength which is lower than the mat strength of the inner layer by at least 1 N when all three layers are measured at a weight per unit area within ten percent of 300 g/m$^2$ and a bulk of 3 cm$^3$/g or less.

4. The absorbent article according to claim 1, wherein the cellulose fluff pulp in the first and second surface layers has a mat strength which is lower than the mat strength of the inner layer by at least 2 N when all three layers are measured at a weight per unit area within ten percent of 300 g/m$^2$ and a bulk of 3 cm$^3$/g or less.

5. The absorbent article according to claim 1, the substance being an inorganic salt.

6. The absorbent article according to claim 1, the substance being a mineral filler.

7. The absorbent article according to claim 1, the substance being a debonder chosen from the group consisting of a quaternary ammonium compounds, bis-imidazolinium compounds, di-quaternary ammonium compounds, polyammonium compounds, phospholipids, silicone quaternaries, organoreactive polysiloxanes and silicone glycols.

8. The absorbent article according to claim 1, the cellulose fibers in at least one of the surface layers having undergone oxidation.

9. The absorbent article according to claim 1, the cellulose fibers in at least one of the surface layers having undergone oxidation by means of an oxidation process using nitroxide.

10. The absorbent article according to claim 1, the cellulose fluff pulp in the inner layer being a chemically produced cellulose fluff pulp (CP).

11. The absorbent article according to claim 1, the absorbent structure having a thickness of at most 8 mm.

12. The absorbent article according to claim 1, the absorbent structure having a thickness of at most 5 mm.

13. The absorbent article according to claim 1, the absorbent structure having a thickness of at most 2 mm.

14. The absorbent article according to claim 1, the absorbent structure having a weight per unit area of 300-2000 g/m$^2$.

15. The absorbent article according to claim 1, the absorbent structure having a weight per unit area of 500-1500 g/m$^2$.

16. The absorbent article according to claim 1, the absorbent structure having a weight per unit area of 800-1200 g/m$^2$.

17. The absorbent article according to claim 1, the inner layer consisting of a mixture of cellulose fluff pulp and 30-90% by weight superabsorbent material.

18. The absorbent article according to claim 1, the inner layer consisting of a mixture of cellulose fluff pulp and 50-90% by weight superabsorbent material.

19. The absorbent article according to claim 1, the structure having a compression pattern.

20. The absorbent article according to claim 1, wherein the absorbent article is a diaper.

21. The absorbent article according to claim 1, wherein the absorbent article is a sanitary towel.

22. The absorbent article according to claim 1, wherein the second surface layer consists essentially of cellulose fluff pulp.

23. The absorbent article according to claim 1, wherein the cellulose fluff pulp in the first surface layer comprises a chemically produced cellulose fluff pulp (CP).

* * * * *